(12) United States Patent
Bjorklund et al.

(10) Patent No.: US 8,043,126 B2
(45) Date of Patent: *Oct. 25, 2011

(54) DEPLOYABLE MEDICAL LEAD FIXATION SYSTEM AND METHOD

(75) Inventors: Vicki L. Bjorklund, Maple Grove, MN (US); John L. Sommer, Coon Rapids, MN (US); Douglas S. Hine, Forest Lake, MN (US); Charles J. Love, Powell, OH (US); Douglas N. Hess, Maple Grove, MN (US); Nicolaas M. Lokhoff, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/816,020

(22) Filed: Jun. 15, 2010

(65) Prior Publication Data

US 2010/0256719 A1    Oct. 7, 2010

Related U.S. Application Data

(62) Division of application No. 11/468,910, filed on Aug. 31, 2006, now Pat. No. 7,736,198.

(51) Int. Cl.
*H01R 13/24* (2006.01)
(52) U.S. Cl. .................................................... 439/700
(58) Field of Classification Search .............. 439/700; 600/375; 607/116, 126, 127
See application file for complete search history.

(56) References Cited

U.S. PATENT DOCUMENTS

| 5,224,491 A | 7/1993 | Mehra |
| 5,279,299 A | 1/1994 | Imran |
| 5,364,340 A | 11/1994 | Coll |
| 5,449,372 A | 9/1995 | Schmaltz et al. |
| 5,456,667 A | 10/1995 | Ham et al. |
| 5,456,705 A | 10/1995 | Morris |
| 5,474,563 A | 12/1995 | Myler et al. |
| 5,653,684 A | 8/1997 | Laptewicz et al. |
| 5,833,707 A | 11/1998 | McIntyre et al. |
| 5,954,761 A | 9/1999 | Machek et al. |
| 6,010,498 A | 1/2000 | Guglielmi |
| 6,014,589 A | 1/2000 | Farley et al. |
| 6,161,029 A | 12/2000 | Spreigl et al. |
| 6,322,559 B1 | 11/2001 | Daulton et al. |
| 6,415,187 B1 | 7/2002 | Kuzma et al. |
| 7,107,105 B2 | 9/2006 | Bjorklund et al. |

FOREIGN PATENT DOCUMENTS

EP    0 861 676    9/1998

OTHER PUBLICATIONS

P0010179.01 (PCT/US2003/029578) PCT Notification of Transmittal of the International Search Report.

*Primary Examiner* — Khiem Nguyen
(74) *Attorney, Agent, or Firm* — Reed A. Duthler

(57) ABSTRACT

An improved medical lead assembly and method of use is provided. The lead assembly includes a lead body, and a spring member positioned adjacent to the lead body. The spring member may be deployed a selectable amount to maintain the lead body in a fixed location within a patient's body. The spring member may be an expandable coil, a mesh structure that is similar to a stent, or any other similar device that may be positioned in a low-profile state during a lead implant procedure. After the lead is positioned at a target destination, the spring member may be deployed an amount that is selected based on the characteristics of the surrounding tissue, including vessel size. According to one aspect of the invention, the lead assembly may provide means for facilitating chronic lead extraction.

20 Claims, 9 Drawing Sheets

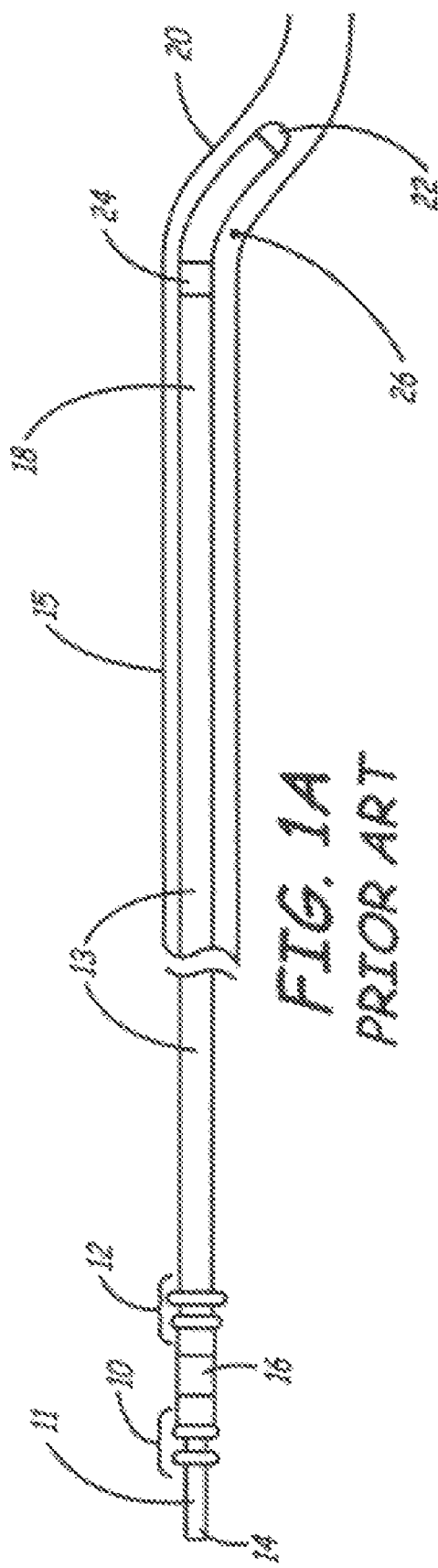
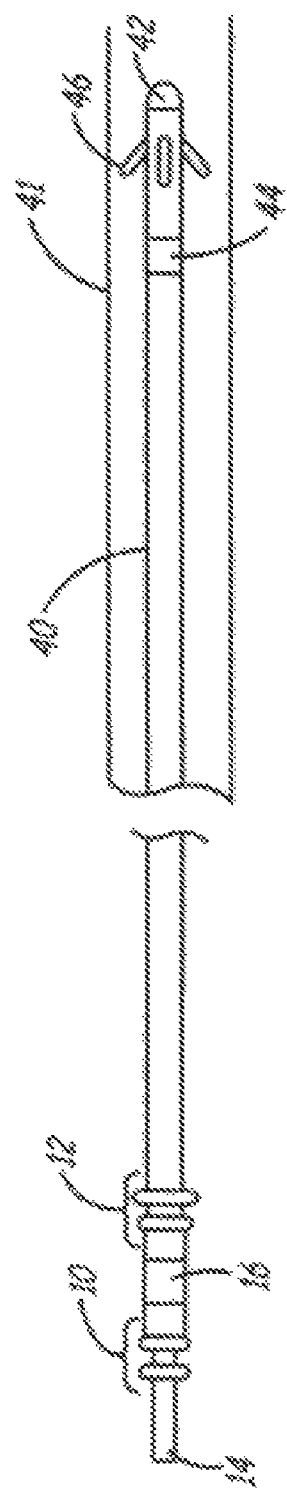
FIG. 1A PRIOR ART
FIG. 1B PRIOR ART

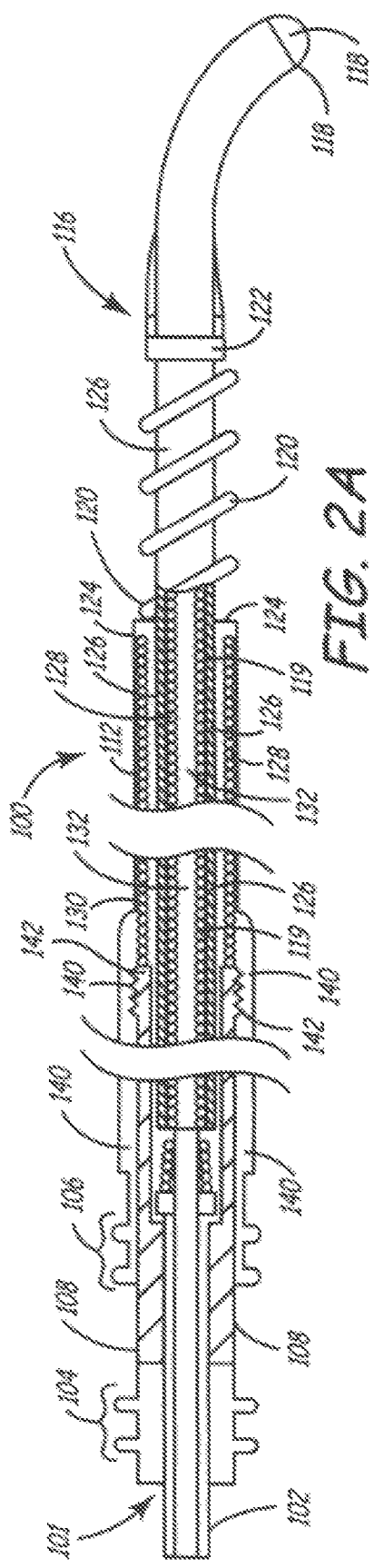
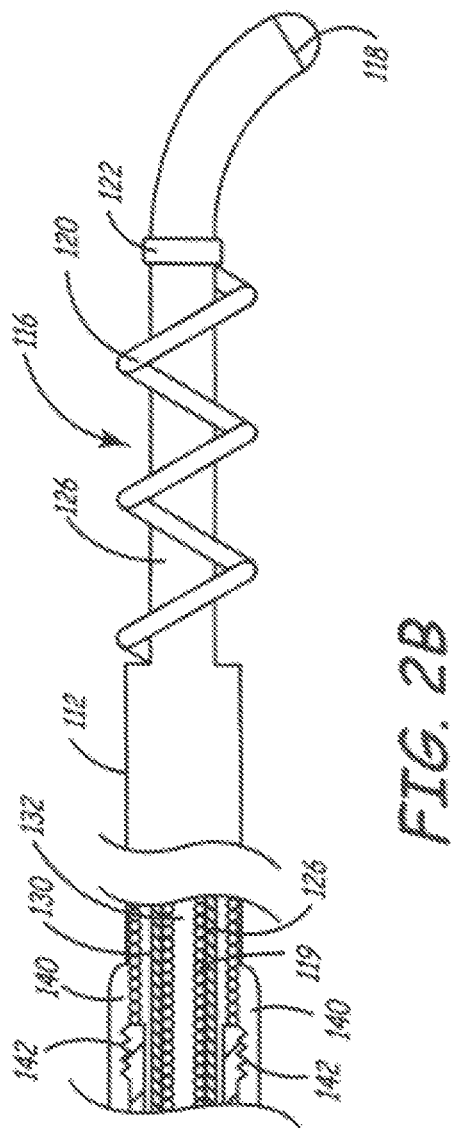

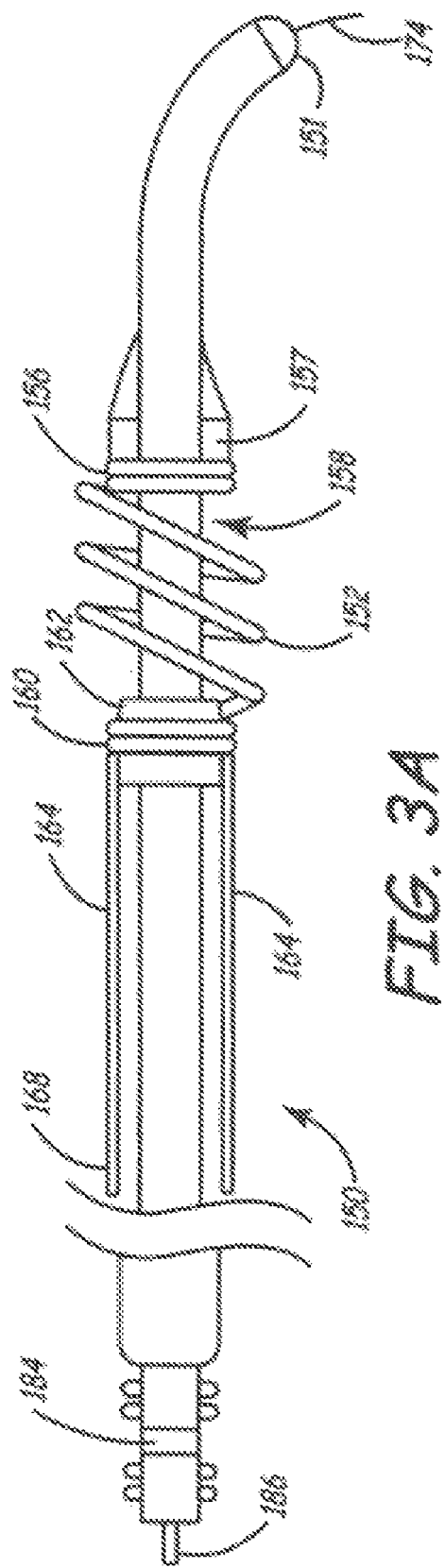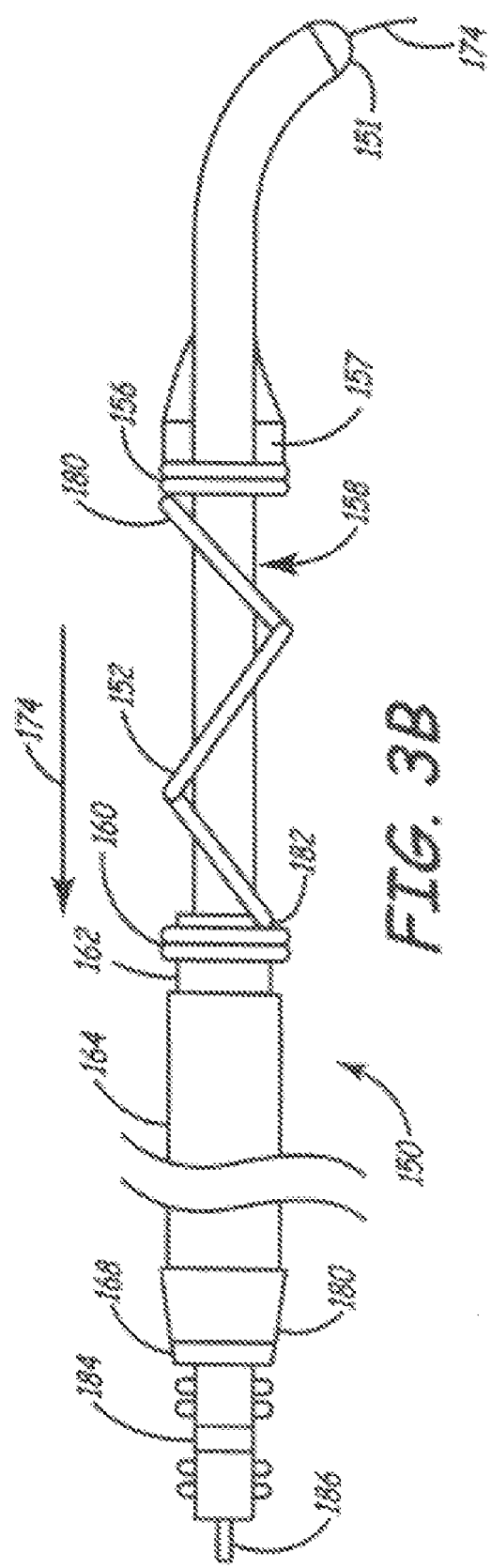

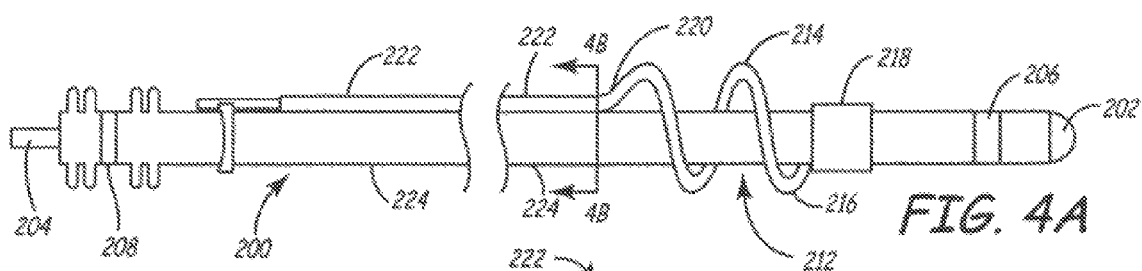
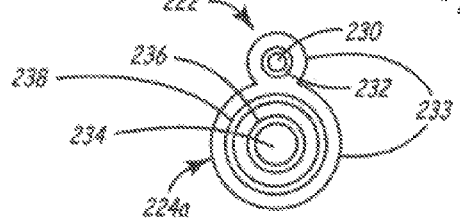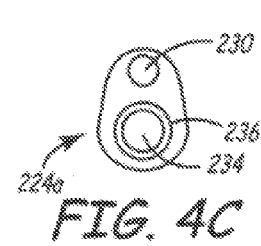
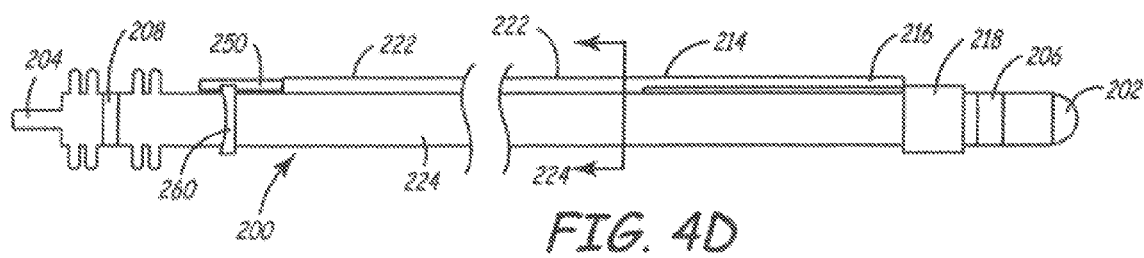

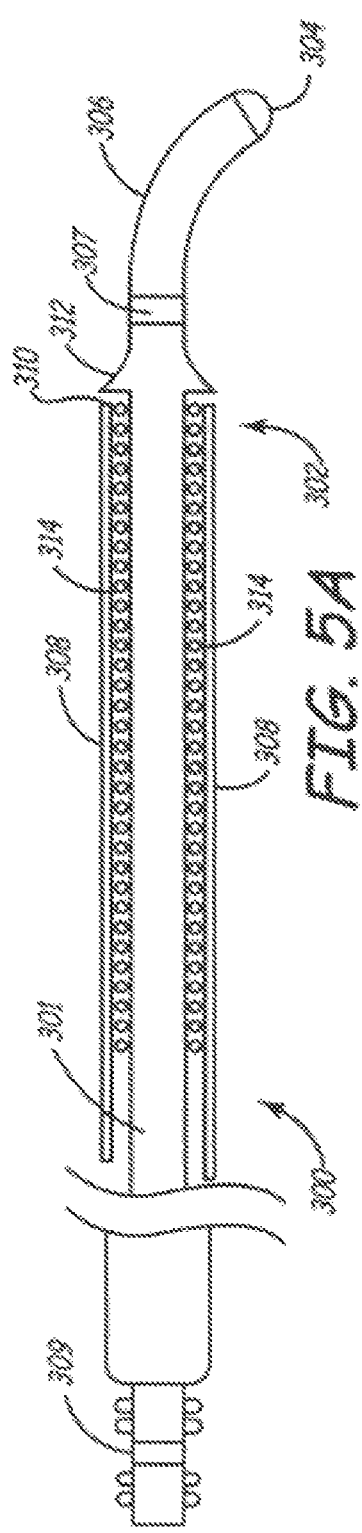
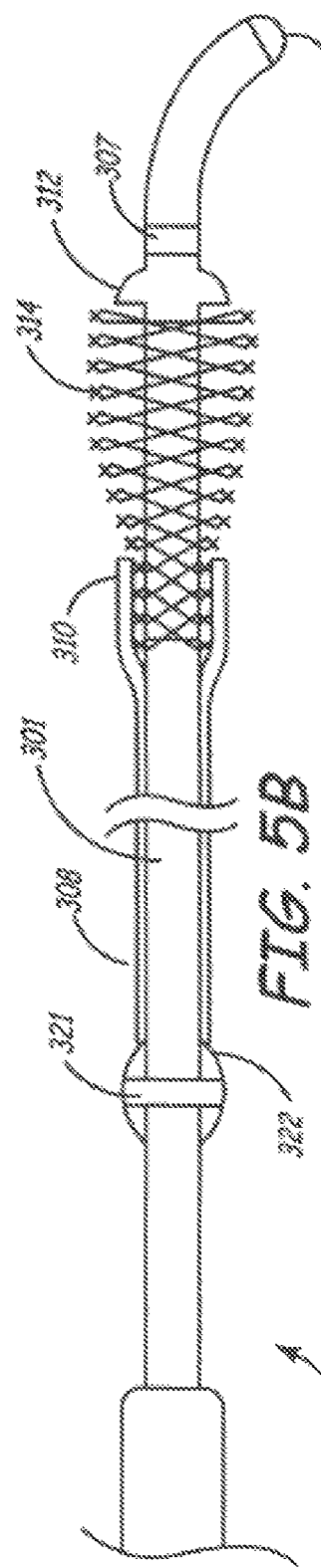
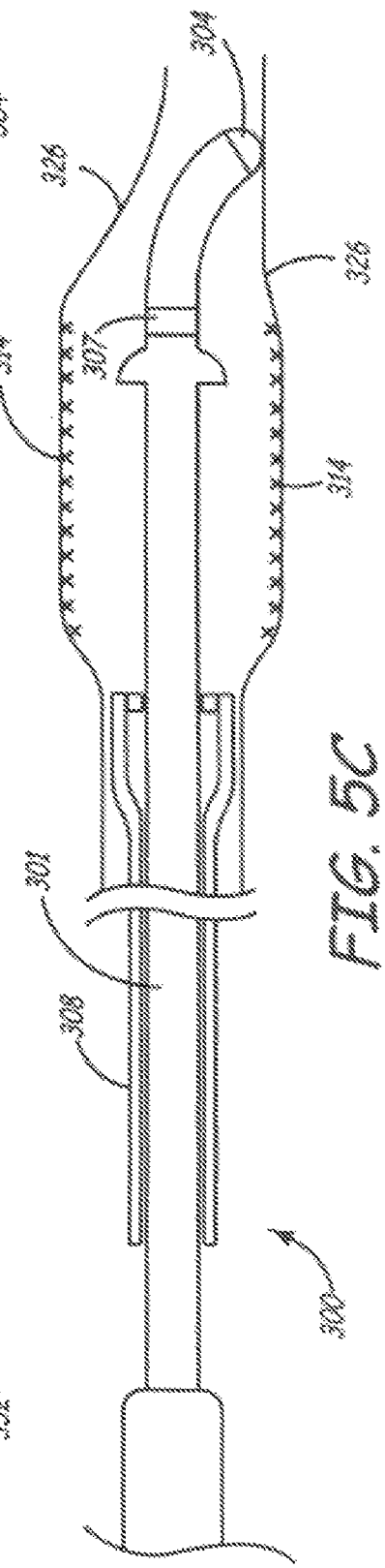
FIG. 5A
FIG. 5B
FIG. 5C

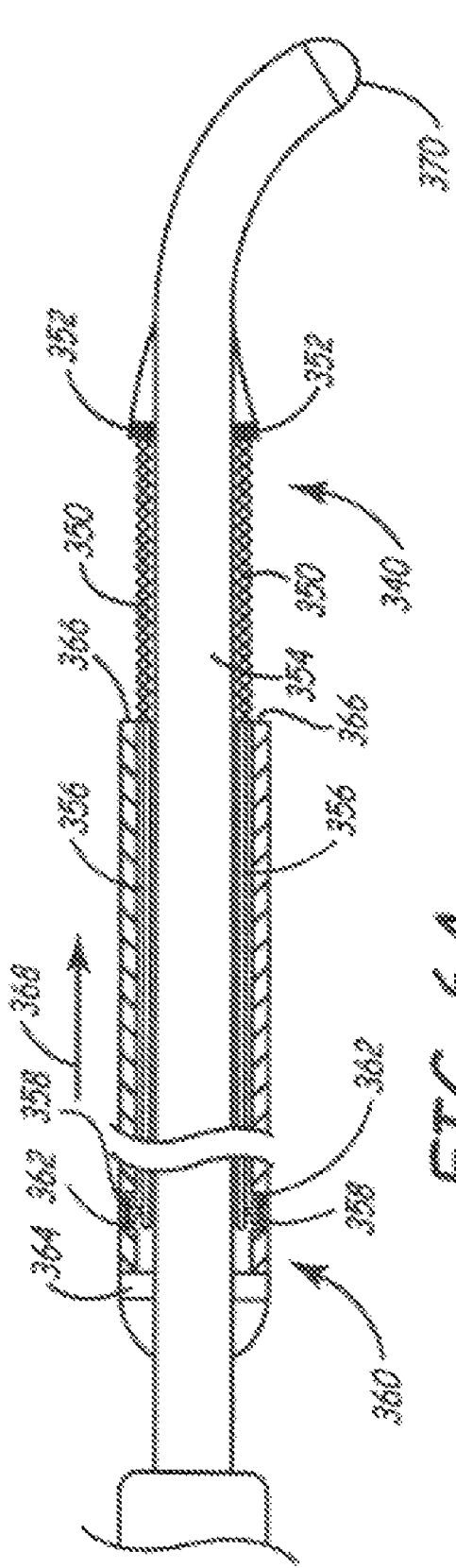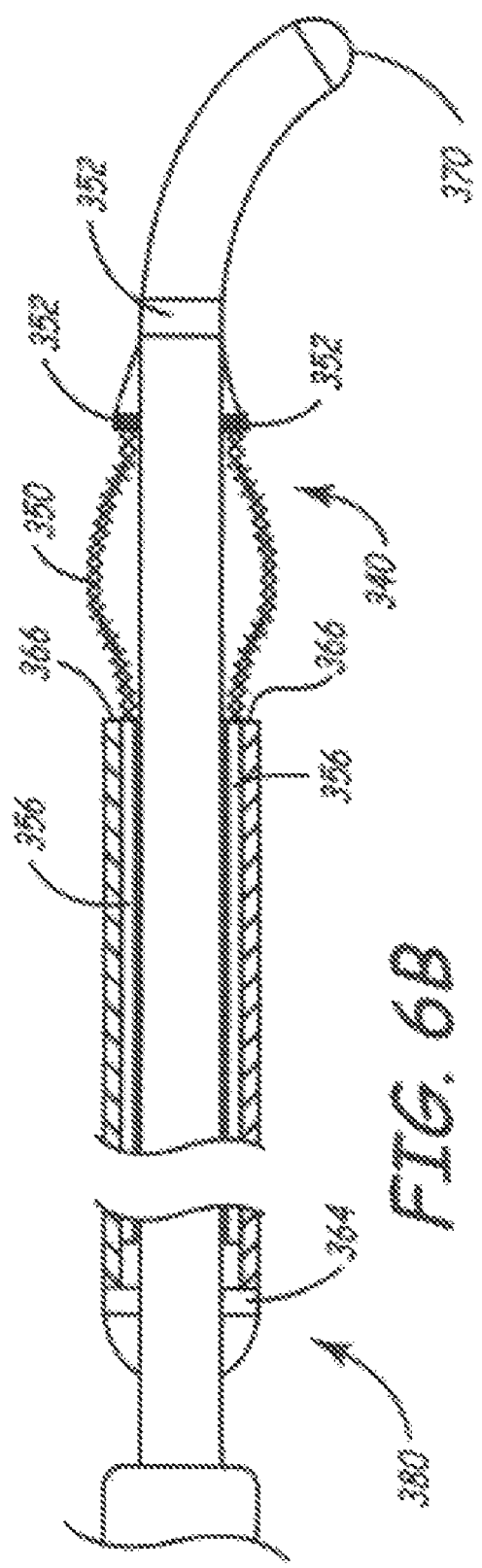

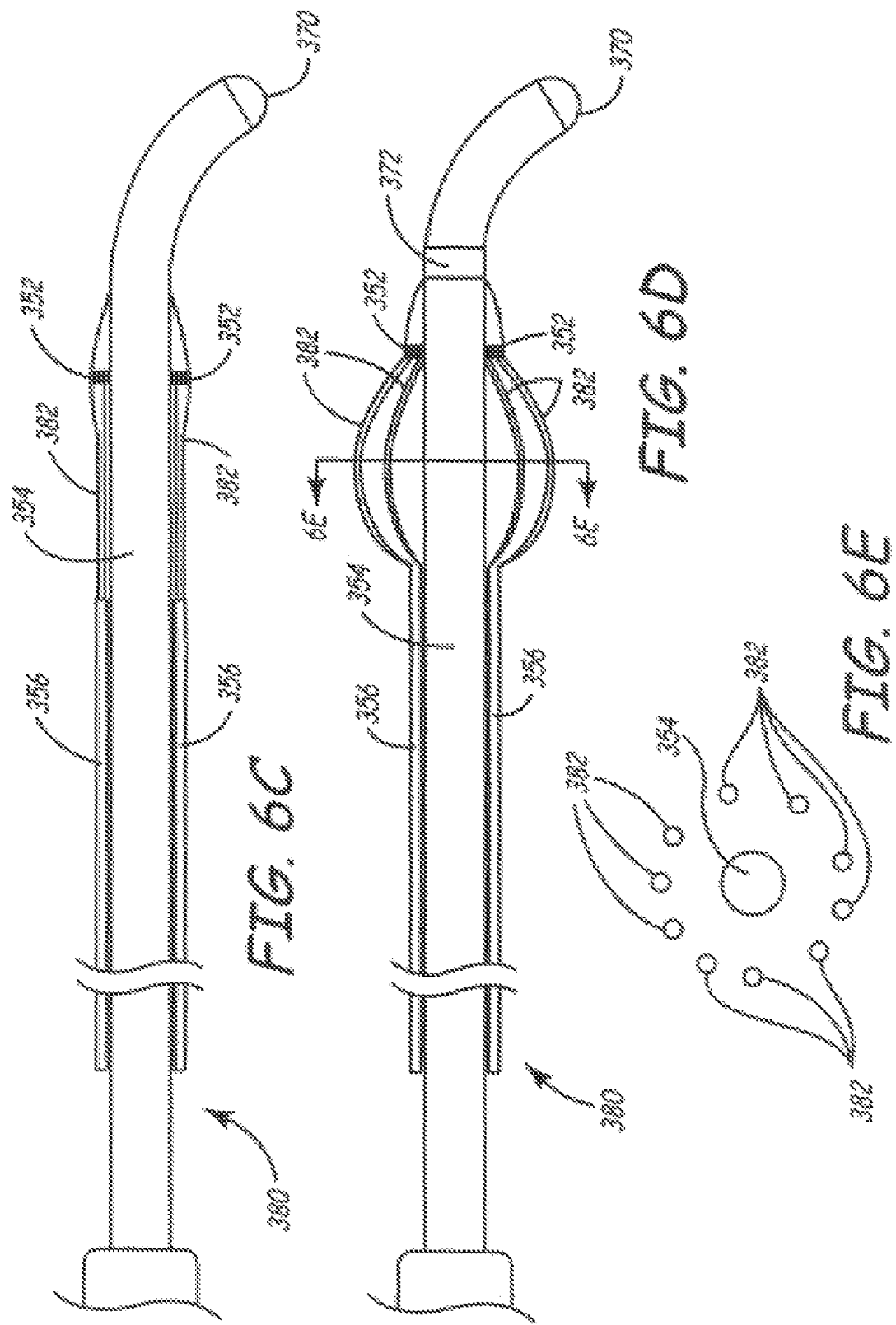

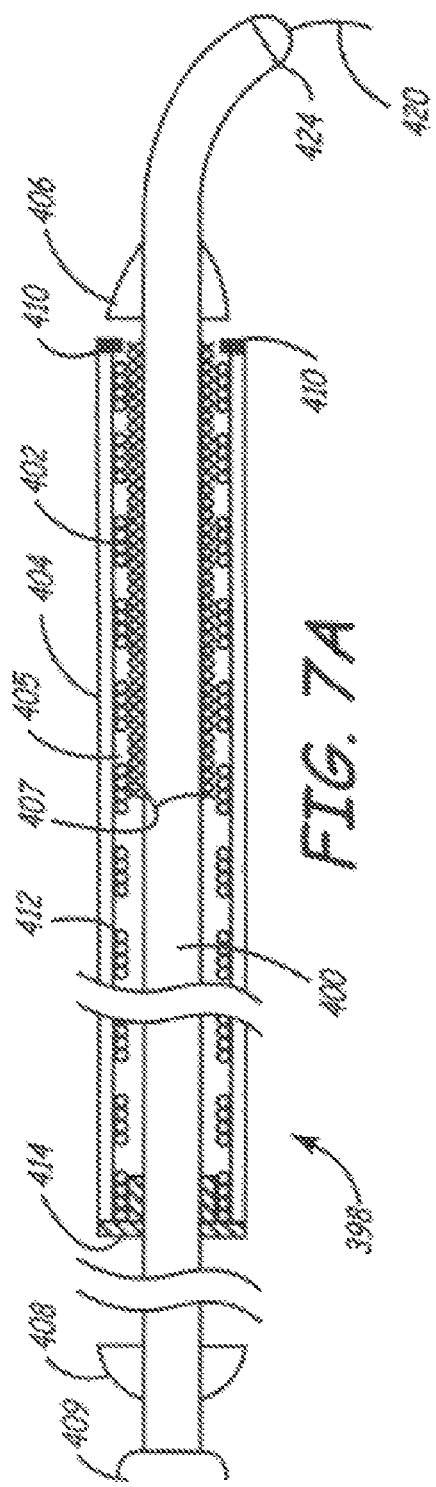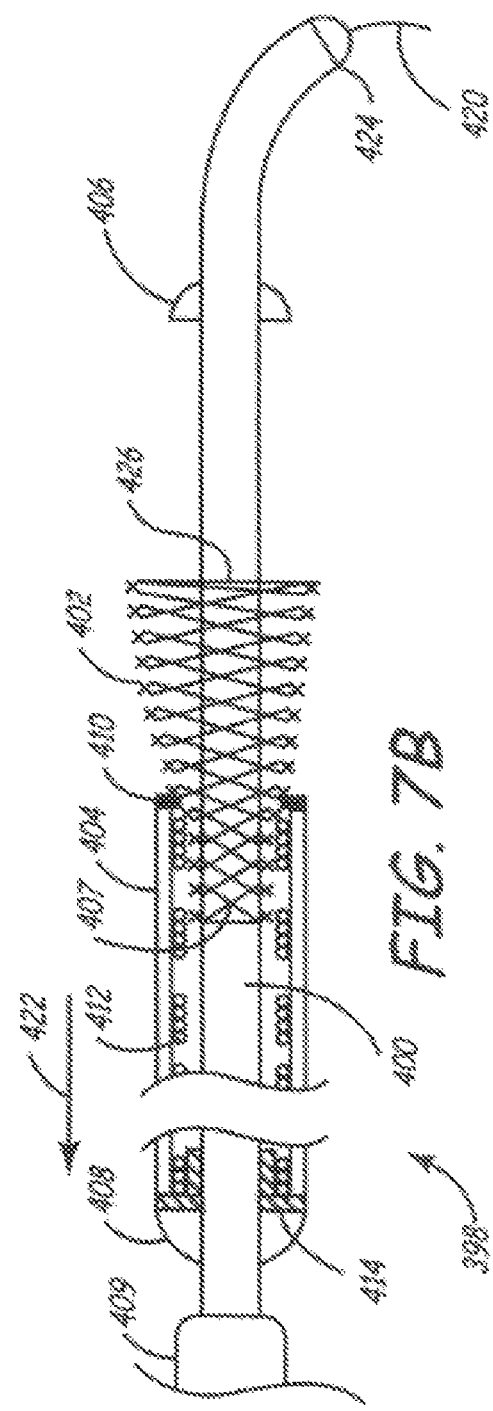

DEPLOYABLE MEDICAL LEAD FIXATION SYSTEM AND METHOD

RELATED APPLICATION

This application is a divisional of U.S. patent application Ser. No. 11/468,910, filed Aug. 31, 2006 entitled "DEPLOYABLE MEDICAL LEAD FIXATION SYSTEM AND METHOD", herein incorporated by reference in its entirety.

FIELD OF THE INVENTION

The present invention relates generally to implanting medical leads within a body and, more particularly, to a system and method for maintaining a medical lead at a site of implant using a deployable fixation mechanism.

BACKGROUND OF THE INVENTION

It is common practice to treat many types of ailments by implanting medical leads within a body. For example, if a person's heart does not beat properly, medical electrical leads may be positioned within the heart or surrounding vessels to deliver electrical stimulation to the heart.

One problem with positioning leads within the body relates to maintaining the leads at a desired location. When a lead is used to deliver an electrical signal to the heart, for example, it is important to maintain the device at a desired position so that the signal will cause desired electrical depolarization of the tissue. If the device shifts position, this desired depolarization may not occur.

The foregoing problem has been addressed by providing a variety of mechanisms for affixing leads to tissue. For example, passive mechanisms such as fixation tines are included at the distal ends of some pacing leads. These types of mechanisms are adapted to engage the trebeculae of the heart so that the lead is fixed in place until tissue begins to grow to further stabilize the device. Other types of active fixation mechanisms such as helical screws may be used to penetrate the tissue to maintain lead positioning.

While the foregoing fixation mechanisms are adequate for affixing a lead within a heart chamber, these methods are not particularly suited for maintaining the position of a lead within a vessel. Although tines may be used to lodge a lead within a vessel, the tines may undesirably block a substantial portion of the blood flow through the vessel. In other cases wherein leads are positioned within large vessels such as the coronary sinus, the tines are often not large enough to extend to the vessel walls to accomplish fixation. Similar problems exist with active fixation mechanisms. For example, a typical helical screw is positioned at the end of a lead such that it is substantially parallel to the walls of a vessel into which the lead has been inserted. This makes fixation using the helix difficult.

One alternative fixation mechanism involves providing an expandable balloon-like structure at the distal end of a lead. When in the expanded state, the balloon contacts the surrounding walls of a vessel to hold the lead in position. This method of fixation occludes the vessel, however, and is therefore not desirable for use in chronic implant situations.

Some of the foregoing problems have been addressed by U.S. Pat. No. 5,954,761 to Machek et al., which discloses a lead assembly that uses one or more stents that expand to contact an inner surface of a body vessel. Once deployed, this type of mechanism may not be retracted, as may be necessary to move the lead to another implant site. Additionally, this type of mechanism makes chronic lead removal difficult, if not impossible, since the stent will become attached to surrounding tissue over time. Finally, the disclosed stent may not be deployed a selectable amount to accommodate vessels of varying sizes.

What is needed, therefore, is an improved system and method for affixing leads within a body that addresses the foregoing problems.

SUMMARY OF THE INVENTION

The current invention provides a lead assembly that includes a lead body, and a spring member positioned adjacent to the lead body. The spring member may be deployed a selectable amount to maintain the lead in a fixed location within a patient's body. The spring member may be an expandable coil, a mesh structure that is similar to a stent, or any other similar device that may be positioned in a low-profile state during a lead implant procedure. After the lead is positioned at a target destination, the spring member may be deployed an amount that is selected based on the size of the surrounding vessel. If necessary, the spring member may be retracted if the lead must be moved to a new destination. The lead assembly may further include means for delivering energy to the spring member to remove in-grown tissue during a chronic lead removal procedure.

According to one embodiment of the invention, the spring member includes a proximal and a distal end, and a collar that slidably engages the lead body. The collar may be coupled to either the proximal or the distal end of the spring member. By positioning the collar at a desired location along the lead body, the spring member may be deployed a selected amount.

In another embodiment, the lead assembly includes a tubular member that may be coupled to the collar or directly to the spring member. The tubular member slidably engages the lead body, and may be positioned relative to the lead body to deploy the spring member a desired amount. A fixation device may be coupled to the tubular member to maintain it in position relative to the lead body. The tubular member may further carry an electrode or optical fibers to deliver ablative energy to tissue during a chronic lead extraction procedure.

In another embodiment, the lead assembly includes a coil that may be unwrapped from around the lead body a desired amount. When in the unwrapped state, the coil provides a means of fixation. The coil may further be employed as an anode. According to one aspect, the coil may be provided with weakened joints that allow the coil to be selectively disengaged from the rest of the lead assembly during a chronic lead extraction procedure.

According to one aspect, a method of positioning a lead assembly within a body is provided. The method includes the steps of providing a lead body that is coupled to a selectably deployable spring member, advancing the lead body to a target location in the body while the spring member is in an un-deployed state, and deploying the spring member a selectable amount to maintain the lead body at the target location.

Other scopes and aspects of the current invention will become apparent from the description set forth below and the accompanying drawings.

BRIEF DESCRIPTION OF THE DRAWINGS

FIG. 1A is a side view of a prior art medical electrical lead.
FIG. 1B is a side view of another prior art medical electrical lead showing a distal end of the lead implanted within a vein.
FIG. 2A is a side, partial cutaway view of one embodiment of a lead according to the current invention.

FIG. 2B is a side plan view of a distal end of a lead showing a spring coil in a deployed state.

FIG. 3A is a side plan view of another embodiment of a lead having a deployable spring member according to the current invention.

FIG. 3B is a side plan view of a lead according to FIG. 3A illustrating the spring member in an elongated position.

FIG. 4A is a side plan view of yet another embodiment of a lead having a deployable spring member according to the current invention.

FIG. 4B is a cross-sectional view of the lead of FIG. 4A at line 4B-4B.

FIG. 4C is a cross-sectional view of another embodiment of the lead of FIG. 4A at line 4B-4B.

FIG. 4D is a side plan view of the lead of FIG. 4A illustrating the spring member in an elongated state.

FIG. 5A is a side plan view of another embodiment of a lead according to the current invention.

FIG. 5B is a side plan view of a lead assembly according to FIG. 5A illustrating spring member in a deployed state.

FIG. 5C is a side plan view of the lead assembly of FIG. 5B illustrating spring member released from the lead.

FIG. 6A is a side view of another embodiment of a lead having a spring that is retained in position by an adjacent tubular member.

FIG. 6B is a side plan view of the lead assembly of FIG. 6A, illustrating the spring in a deployed state.

FIG. 6C is a side plan view of an embodiment of a lead assembly similar to that shown in FIG. 6A, and including a spring formed of multiple flexible strands.

FIG. 6D is a side view of the lead assembly of FIG. 6C illustrating the spring in a deployed state.

FIG. 6E is a cross-sectional view of the lead assembly of FIG. 6D at line 6E-6E.

FIG. 7A is a side plan view of a lead that is similar to the embodiment shown in FIGS. 6A and 6B.

FIG. 7B is a side plan view of the lead of FIG. 7A illustrating the spring in a fully deployed state.

DETAILED DESCRIPTION OF THE PREFERRED EMBODIMENTS

Figures 5D, 5E:
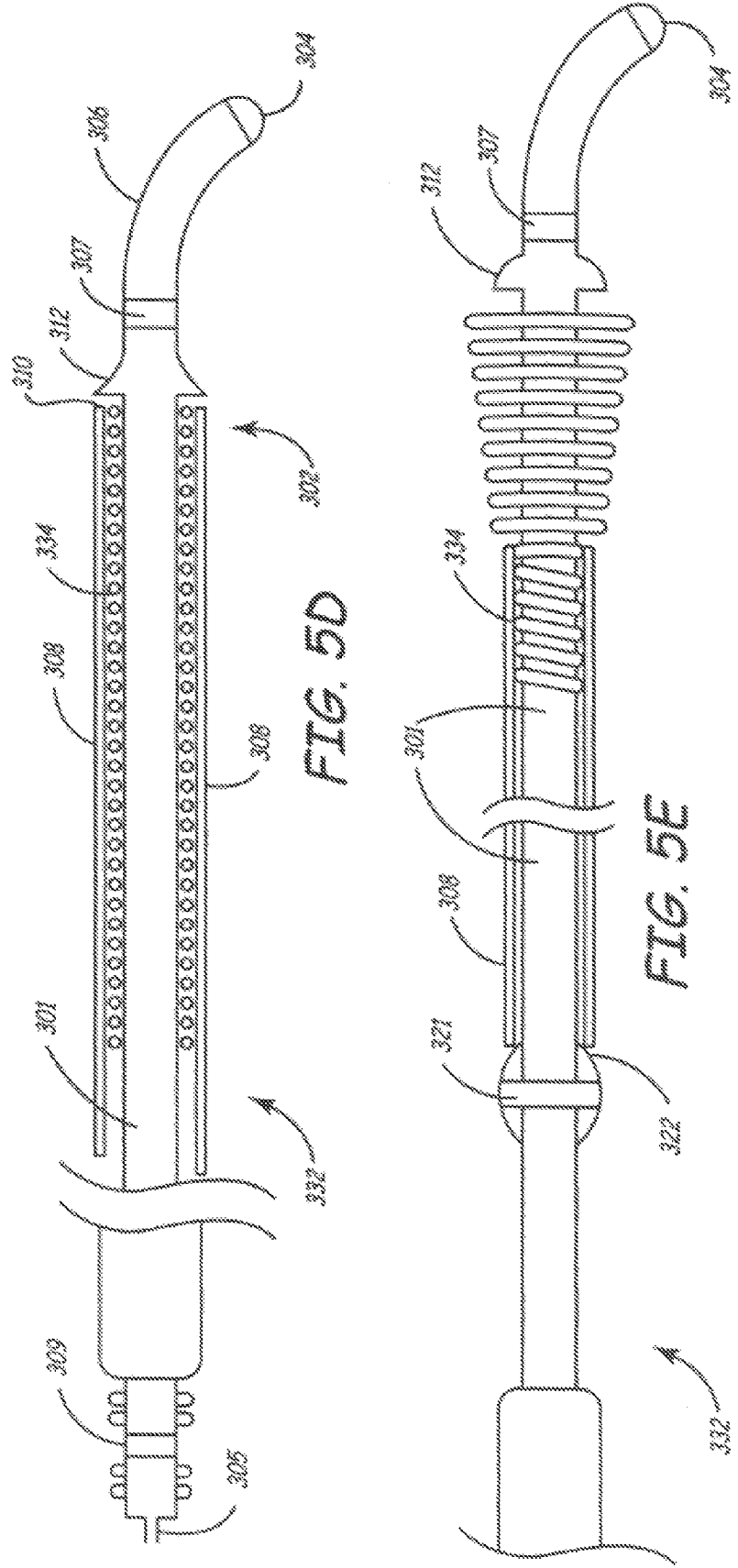
FIG. 5D is a side plan view of a lead assembly that is similar to that shown in FIG. 5A, and that includes a coil as the spring member.
FIG. 5E is a side plan view of the lead assembly of FIG. 5D, illustrating spring member in a deployed state.

FIG. 1A is a side view of a prior art medical electrical lead. The lead has a proximal end 11 including pairs of sealing rings 10 and 12, a pin connector 14, and a ring connector 16. The lead further includes a lead body 13 that may be formed of a biocompatible material such as polyurethane or silicone. A distal end 18 of the lead, which is shown implanted within a vein 20, includes a tip electrode 22 and a ring electrode 24. A curve 26 is provided to wedge distal end within vein 20, and to further urge tip electrode 22 against tissue. If a vein 15 is large, however, as is the case in FIG. 1A, the curve is not large enough to provide adequate fixation of the lead within vein 15.

FIG. 1B is a side view of another prior art medical electrical lead showing a distal end 40 of the lead implanted within a vein 41. Distal end 40 includes a tip electrode 42, optional ring electrode 44, and traditional fixation tines 46. In a manner similar to that shown in FIG. 1A, fixation tines 46 do not provide adequate fixation when distal end 40 is positioned within a large vessel. Additionally, the tines may hinder site selection during lead placement.

As discussed above, prior art lead fixation mechanisms are not particularly adaptable to all vessel sizes and shapes. Moreover, these fixation mechanisms may, in some cases, make lead placement more difficult. The current invention addresses these problems by providing a spring mechanism that may be selectively deployed to accommodate all types of anatomy. Because the spring mechanism is deployable, it may be in a retracted state during implantation so that the lead distal end may be easily positioned at the target site.

FIG. 2A is a side, partial cutaway view of one embodiment of a lead 100 according to the present invention. The lead of this embodiment includes a proximal end 101 having a pin connector 102, corresponding pairs of sealing rings 104 and 106, and an optional ring connector 108. The lead body has a biocompatible outer jacket 112 that may be formed of a material such as polyurethane, silicone, or any other type of biocompatible polymer suitable for this purpose. Lead 100 further includes a distal end 116 having a tip electrode 118 electrically coupled to pin connector 102 via a conductive coil 119.

Proximal to tip electrode 118 is a spring coil 120 that is preferable formed of a shape memory alloy such as Nitinol, or a biocompatible material having a low Young's modulus so as to exhibit spring-like characteristics. Spring coil 120 is coupled at its distal end to a stationary collar 122 that is retained in a fixed position relative to distal end 116. Spring coil 120 is further coupled at its proximal end to a rotating member 124. Rotating member is mechanically coupled to outer jacket 112, both of which may be rotated with respect to inner jacket 126 in a manner to be discussed below. Rotating member may optionally be designed to prevent fluid ingress into an interior chamber 128. Inner jacket 126 may extend from pin connector 102 to tip electrode 118, and may be formed of a same, or different biocompatible material, as compared to outer jacket 112.

In a multi-polar embodiment of lead 100, a coil 130, which may be single or multi-filar, is positioned around inner jacket 126 within interior chamber 128 and is mechanically coupled to rotating member 124. Coil 130, which is formed of a biocompatible conductive material such as stainless steel, extends to a ring connector 108 at proximal end 101 of lead 100. The coil may be electrically coupled to ring connector 108 via a conductive threaded collar 142 as will be discussed below. If coil 130 is electrically coupled to ring connector 108, rotating member 124 may be formed of an electrically conductive material to serve as the anode. In this embodiment, spring coil may be formed of a non-conductive material, or may be electrically isolated from rotating member. Alternatively, spring coil 120 may be formed of an electrically conductive material, and may be electrically coupled to rotating member to extend the length of the anode. In a unipolar embodiment of lead 100, coil 130 and ring connector 108 may be omitted.

During a lead implant procedure, spring coil 120 is wound tightly around jacket. This allows distal end 116 of lead 100 to be delivered to a target location within the lumen of a guide catheter. In one embodiment of the invention, lead 100 includes a central lumen 132 to receive a guiding device such as a stylet that may be used to aid in positioning distal end 116 at the target destination. Central lumen 132 may extend through tip electrode 118 so that the lead may be delivered over a guidewire.

According to the current invention, threaded collar 142 is mechanically coupled to connector sleeve 140 and outer jacket 112 using, for example, a medical grade adhesive. Threaded collar 142, which may be formed of a conductive material, may further be mechanically and electrically coupled to coil 130 using a crimp, weld, or other coupling mechanism. In the embodiment shown, threaded collar 142 includes a crimp sleeve at its distal end to crimp to coil 130. Threaded grooves of ring connector 108 are provided to rotatably interface to threaded collar 142. When connector sleeve 140 is rotated with respective to the grooves of ring connector 108, threaded collar 142 is advanced distally with respective to ring connector, causing the exposed portion of ring connector 108 to lengthen, and unwinding spring coil 120 from around distal end 116 of lead body. If threaded collar 142 is formed of a conductive material, coil 130 remains electrically coupled to ring connector 108 as threaded collar is advanced so that rotating member 124 and optionally, spring coil 120, may be employed as an anode.

FIG. 2B is a side plan view of distal end 116 of lead 100 showing spring coil 120 in a deployed state. As noted above, when deployed, threaded collar 142 is advanced distally with respect to the grooves of ring connector 108. Some form of a stop member may be provided on threaded collar 142 and/or ring connector 108 to prevent the threaded collar 142 from being advanced too far. In this state, spring coil 120 is expanded to readily contact tissue such as the walls of a vessel to stabilize distal end 116 at the target implant location. Spring coil 120 may be retracted by counter rotating connector sleeve 140 with respect to ring connector 108, as may be required to reposition the lead.

One or more elements of lead 100 may be formed of a material that is visible under a fluoroscope. For example, in an embodiment wherein spring coil 120 is insulated with a polymer, the polymer may be loaded with a fluorovisible material such as $BaSO_4$. In another embodiment, spring coil 120 may formed of a conductive material such as a shape memory alloy that includes platinum, which has a higher visibility under a fluoroscope. This allows an implanting physician to more readily determine the extent to which spring coil 120 has been unwound within the body.

FIG. 3A is a side plan view of another embodiment of a lead 150 according to the current invention. Lead 150 has a distal end 158 that includes a spring 152 formed of a shape memory alloy such as Nitinol, or a material having a low Young's modulus. Spring 152 has a distal end 156 that may be wound around distal end 158 of lead. The lead body may include a ridge 157 or other type of stop member to maintain distal end 156 of spring 152 at a desired location. Distal end 156 may further be affixed to the lead body using a medical grade adhesive, a staking operation, and/or other coupling mechanisms.

Spring 152 includes a proximal end 160 that is maintained in a fixed position relative to a collar 162. Proximal end 160 may further be wound around, and/or crimped, staked or otherwise affixed as by medical grade adhesive to collar 162. In one embodiment, collar 162 includes a channel to aid in maintaining, all, or a portion of, proximal end 160 of spring 152 in a fixed position.

Collar 162, which may be formed primarily of a biocompatible tubing material such as polyurethane, is slidably mounted on distal end 158 of lead body. A hydrophilic coating such as polyacrylamide or another lubricious substance may be applied to an inner surface of collar 162 to allow it to slide along lead body with a minimum amount of friction. Collar may be loaded with $BaSO_4$ or may be formed of a platinum alloy so that it is visible when using a fluoroscope.

Collar 162 is coupled to, or may be integrally formed with, tubular member 164 (shown in cross-section). Tubular member may be formed of a polyurethane tubing that is similar to that used to form collar 162. Tubular member may further have some, or all, of its internal surface coated with a hydrophilic substance. In one embodiment, collar may be eliminated entirely, with spring 152 being coupled directly to tubular member. In this embodiment, however, the lead assembly will not be substantially isodiametric along its length, which is preferred for both lead delivery and chronic lead extraction.

FIG. 3A shows spring 152 in a resting state. In this position, the diameter of spring 152 is larger than the diameter of the lead body, and proximal end 168 of tubular member 164 is located somewhat distal to the lead connector.

FIG. 3B is a side plan view of lead 150, illustrating spring 152 in an elongated position. This position is achieved by pulling tubular member 164 (shown in plan view in FIG. 3B) in a proximal direction relative to lead body as indicated by arrow 174. This, in turn, pulls collar 162 and distal end 160 of spring 152 in a proximal direction, causing spring 152 to become extended. In a fully extended position, spring 152 is close to, or substantially flush with, the outer surface of distal end 158 of lead body so that passage of the lead is not obstructed during an implant procedure. The extended spring position may be maintained during an implant procedure by positioning a removable clip 180 over the proximal end 168 of tubular member 164. Lead 150 may further be provided with a tapered distal tip to further aid in passage of the lead through the vessels of a body.

As discussed above with respect to FIGS. 2A and 2B, the lead of FIGS. 3A and 3B may be implanted using a guide catheter. In an embodiment wherein lead 150 includes an internal lumen, lead placement may be further aided by the use of a stylet or another type of stiffening member. Lead 150 may include a lumen that extends through distal tip electrode 151, allowing for the use of a guidewire 174.

After the lead is at a target destination, spring 152 may be allowed to resume the resting position shown in FIG. 3A. In another embodiment, the spring may be deployed in an intermediate state that is between a fully extended and a resting state. This can be accomplished by maintaining proximal end 168 of tubular member 164 at a desired location relative to the lead body using a clip or other removable fastening member. In either case, the enlarged diameter of spring 152 maintains lead at the desired implant position.

It may be noted that although FIG. 3A shows central axis of spring 152 to be substantially aligned with the central axis of lead body when the spring is in a resting state, this need not be the case. Spring 152 may extend farther on one side of the lead than another to aid in forcing a tip electrode 151 against tissue when the lead is implanted within a vessel.

In one embodiment of lead 150, spring 152 includes weakened joints 180 and 182 at distal end 156 and proximal end 160, respectively, that are designed to fracture when sufficient force is applied. This may be desirable to aid in chronic lead extraction. For example, weakened joint 182 may be weaker than weakened joint 180. When tubular member 164 is rotated or pulled in a proximal direction during a lead explant procedure, weakened joint 182 fractures. Tubular member 164 may then be slid in a distal direction so that collar 162 is adjacent distal end 156 of spring 152. If ridge 157 has a diameter smaller than inner diameter of collar 162, the lead may be pulled in a proximal direction while force is applied to tubular member 164 in a distal direction. This causes weakened joint 180 to fracture, allowing lead 150 and tubular member 164 to be removed from the body, while leaving spring 152 within a vessel.

According to another aspect of the current embodiment, spring 152 may be electrically coupled to a ring connector 184 for use as an anode. This could be accomplished by providing a conductive cable or coil to electrically couple ring connector 184 to stationary distal end 156 of spring 152. If desired, only a portion of the spring, such as the turns at distal end 156, may be selected to serve as the anode, with the remainder of the spring being electrically insulated. Pin connector 186 is coupled to tip electrode 151, which serves as the cathode.

FIG. 4A is a side plan of yet another embodiment of a lead 200 according to the present invention. The general configuration of lead 200 is similar to that discussed above. Specifically, lead 200 includes a tip electrode 202 that is electrically coupled to pin connector 204. An optional ring electrode 206 may be coupled to ring connector 208 for multi-polar embodiments.

In this embodiment, lead 200 includes a distal end 212 having a spring member 214. Spring member may be formed of a polymer such as polyurethane that has been permanently shaped. Alternatively, spring member may include a coil formed of shape memory alloy, or a material having a low Young's Modulus. In a resting state, spring member 214 assumes a helical configuration surrounding, and having a diameter larger than, distal end 212.

Spring member 214 has a distal end 216 coupled to a collar 218. Collar 218, which may be a ring formed of biocompatible tubing material, slidably engages distal end 212 of lead 200. The interior surface of collar 218 may be coated with polyacrylamide or another hydrophilic slip-coating material to provide a lubricious surface that slides easily along distal end 212 of lead 200.

A proximal end 220 of spring member 214 is coupled to a side lumen 222. Side lumen is positioned adjacent one side of lead body 224.

FIG. 4B is a cross-sectional view of lead 200 of FIG. 4A at line 4B-4B. This view illustrates side lumen 222, which includes a coil 232 that is used to form one embodiment of spring member 214 in the manner discussed above. Coil 232, which defines internal lumen 230, is adjacent to an insulative jacket 233. Jacket 233 may be formed of any biocompatible polymer such as silicone or polyurethane.

Side lumen 222 may be integrally formed with lead body 224 as shown in FIG. 4B or may be affixed thereto as by a medical grade adhesive. Lead body 224 may include a central lumen 234 to receive a guiding device such as a stylet or a guidewire to aid in lead placement. In one embodiment, central lumen 234 extends through tip electrode 202 to allow for over-the-wire lead placement as discussed above. Lead body 224 is further shown to include a coil conductor 236, which electrically couples tip electrode 202 to pin connector 204. A second coil 238 electrically couples optional ring electrode 206 to ring connector 208.

FIG. 4C is a cross-sectional view of another embodiment of lead 200. In this embodiment, lead body 224a is an oval shape to include internal lumen 230 and coil conductor 236. Optional coils 232 and 239 are omitted in this view.

FIG. 4D is a side plan view of the lead of FIG. 4A illustrating spring member 214 in an elongated state. To achieve this position, a stiffening stylet 250 is inserted within side lumen 222 through coil 232 of spring member 214. Force is exerted in a distal direction to cause collar 218 to slide towards tip electrode 202. As spring member 214 is extended, collar 218 rotates until spring member is in a substantially straightened position, and rests relatively close to the outer surface of lead 200. This position of the stiffening stylet within side lumen may be maintained during lead placement using a clip 260 or another removable fixation device. Stylet 250 may be used in conjunction with a stylet or guidewire inserted within central lumen 234 to enhance steerability during lead placement.

In one embodiment, a small lumen opening at distal end 216 of spring member allows a guidewire or a tip portion of a stylet to be inserted through side lumen 222 and out the opening. The guidewire or stylet may be used along with a second guidewire inserted within central lumen 234 to aid in navigation during lead implant. In this embodiment, the proximal end of the guidewire or stylet has a larger circumference than the distal portion to act as a stopper when that larger portion reaches the opening at distal end 216 of spring member 214. This allows the implanting physician to exert force on the guidewire or stylet to straighten the spring memory after a predetermined portion of the guidewire or stylet tip has exited the lumen.

As will be appreciated, the configuration shown in FIG. 4D allows lead 200 to be positioned within the body without the interference of spring member 214. The lead may be implanted using a guide catheter, and/or an additional guiding device such as a stylet or guidewire.

After tip electrode is positioned at a desired implant location, stylet 250 may be removed from side lumen 222 to allow spring member 214 to assume a resting position. In another embodiment, the position of stylet 250 may be adjusted with respect to lead body 224 so that spring member 214 assumes a configuration having a desired diameter. In this manner, the diameter of spring member 214 is tailored to accommodate the size of a particular vessel. A selected position of stylet 250 may be maintained using a removable fastening device. In one embodiment, stylet may be provided with permanently affixed clips or other connection members for this purpose. In another embodiment, stylet may include clamps such as clamp 260 to engage lead body 224. Any other type of connection member may be integrated with stylet and/or lead body to aid in affixing stylet at a desired location with respect to lead body 224.

FIG. 5A a side plan view of another embodiment of a lead assembly 300 according to the current invention. Lead 301 includes a distal end 302 having a tip electrode 304, and a curved portion 306 designed to urge tip electrode into communication with tissue, as discussed above. Tip electrode 304 is electrically coupled to pin connector 305. An optional ring electrode 307 may be coupled to ring connector 309 in multi-polar embodiments.

In the embodiment of FIG. 5A, a tubular member 308 (shown in cutaway view) that may be formed of a biocompatible polymer tubing similar to that discussed above is slid over lead 301. An inner surface of tubular member 308 may be coated with a hydrophilic coating such as polyacrylamide to minimize the friction between tubular member and the lead body. When in a fully extended position, a distal end 310 of tubular member contacts a stopper mechanism provided by ridge 312. A spring member 314 (also shown in cutaway view) is positioned between lead 301 and tubular member 308 in a compressed state. Spring member 314 may be formed of a mesh similar to that used in implantable stents, or may be any type of spring-like structure including an expandable coil.

A configuration such as shown in FIG. 5A is employed during an implant procedure to position spring member 314 at a selected destination in a patient's body. This may be accomplished by delivering lead assembly 300 through a lumen of a guide catheter, and/or by using a delivery mechanism such as a guidewire or stylet that is inserted within an inner lumen of lead 301. Upon reaching a target implant destination, tubular member 308 is pulled in a proximal direction to allow spring member 314 to expand. The amount of deployment of spring member 314 is controlled by the distance tubular member is moved in the proximal direction.

In one embodiment, distal end of tubular member 308 may include a deployment indicator that is formed of a fluorovisible material such as an shape memory alloy including platinum, or a polymer loaded with a fluorovisible substance. In addition, ridge 312, spring member 314, and/or some other element located on the distal end of lead assembly 300 may include a fluorovisible material. This allows an implanting physician to determine the amount of deployment of spring member 314.

FIG. 5B is a side plan of lead assembly 300, with tubular member of FIG. 5A shown in cutaway view. This view shows partial deployment of spring member 314, which in the exemplary embodiment is an expandable mesh structure. In this embodiment, stopper 321, which may be integrally formed with lead body, or may be a removable clip-like structure, is provided at the lead proximal end. Stopper 321 limits the proximal movement of tubular member 308. When proximal end 322 of tubular member rests against stopper 321, spring member 314 is in a predetermined, fully deployed state. By selectively positioning proximal end of tubular member 308 at an intermediate position relative to stopper 321, or by re-positioning the stopper itself, the extent of deployment of spring member 314 may be controlled. Spring member 314 may be re-captured by moving tubular member 308 in a distal direction relative to lead body. This may be necessary to re-position the lead to a new implant location.

FIG. 5C illustrates an embodiment of the lead of FIG. 5B wherein stopper 321 has been removed. Tubular member has been pulled beyond the position occupied by stopper 321 to allow spring member 314 to be released into vessel 326. This may be desirable to aid in lead explant.

FIG. 5D is a side view of a lead assembly 332 that is similar to that shown in FIG. 5A, with similar elements being labeled with like numerical designators. In this embodiment, spring member 334 is an expandable coil (shown in cross-section.) Tubular member 308 (also shown in cross-section) retains spring member 334 adjacent lead 301 during the implant procedure.

FIG. 5E is a side view of the lead assembly of FIG. 5D, illustrating spring member 334 (shown in plan view) in a deployed state. Spring member 334 is deployed by pulling tubular member 308 in a proximal direction relative to lead 301. In a manner similar to that described above in reference to lead assembly 300, spring member 334 may be released from lead 301 by removing stopper 321 and pulling tubular member 308 in a proximal direction. This provides a means to remove a chronically implanted lead from the body during an explant procedure.

FIG. 6A is a side view of another embodiment of a lead 340 according to the current invention. Lead 340 includes a spring 350 which may be a mesh structure similar to a stent, a coil, or some other type of expandable member. In this embodiment, spring 350 (shown in cross-section) is coupled at a distal end to a stationary collar 352 using any of the fixation mechanisms discussed above. Stationary collar is in a fixed position relative to lead body 354. A proximal end of spring 350 is coupled to a slidable tubular member 356 (also shown in cross-section), which may be formed of any biocompatible polymer tubing in a manner similar to that discussed above. Tubular member may be coated on an inner surface with a hydrophilic coating to allow it to slide more freely over lead body 354. Proximal end of tubular member 356 includes one or more coupling devices 358 as will be described below.

The assembly of FIG. 6A further includes a generally tubular extraction device 360 shown in cross-section that is provided to facilitate chronic lead removal. Extraction device 360 includes slots 362 that are designed to mechanically lock with the one or more coupling devices 358 when extraction device 360 is rotated relative to tubular member 356. Any other type of locking mechanism may be used in the alternative. When in the locked state, extraction device 360 and tubular member 356 may be moved as a unit with respect to lead body 354.

FIG. 6A illustrates spring 350 in an un-deployed state. This configuration may be used to implant the lead within a patient's body. Thereafter, a force may be exerted on proximal end of extraction device 360 to cause the device and tubular member 356 to be slid in a distal direction relative to lead body 354 as shown by arrow 368. This causes spring 350 to bow in an outward direction, thereby retaining the lead at a desired implant site.

FIG. 6B is a side view of the lead of FIG. 6A, illustrating spring 350 in a deployed state. If desired, extraction device 360 and tubular member 356 can be selectably positioned relative to lead body 354 to deploy spring a desired about. This position may be maintained using a removable clip in the manner discussed above. In one embodiment, spring may be formed of, or loaded with, a fluorovisible material to aid the implanting physician in determining the amount of deployment.

Lead 340 includes a tip electrode 370, and may further include an optional electrode 372 shown as a ring electrode in FIG. 6B. Electrode 372 may take any other suitable geometric shape, and may optionally be a flexible coil. If desired, collar 352 may be formed of a conductive material to serve as the anode. In yet another embodiment, all, or a portion of spring, is formed of conductive material to serve as the anode.

As noted above, extraction device 360 is provided to facilitate chronic lead removal. During an extraction process, extraction device is counter rotated with respect to tubular member 356 so that the extraction device may be moved independently of the tubular member. According to one aspect of the invention, extraction device 360 includes a connector 364 at its proximal end. Multiple optical fibers may be provided to extend from connector 364 to a distal end 366. These fibers are aligned substantially parallel to, and encircle, the longitudinal axis of the device. In one embodiment, approximately eighty optical fibers are used, each having a fiber core diameter of approximately 100 micrometers. When connector 364 is coupled to a source of photo-ablative excimer laser energy, short bursts of laser energy may be delivered via the optical fibers at a repetition rate of between 25 and 40 Hz to burn away tissue coupled to spring 350. An energy setting of between 35 and 60 microjoules per square millimeter is recommended in this embodiment. Extraction device 360 may be gradually slid in a distal direction relative to tubular member 356 and spring 350 to remove tissue from the entire surface of spring. Tubular member 356 may then be coupled to extraction device 360 in the manner discussed above so that the interconnected assembly may be pulled in a proximal direction to flatten spring 350. The lead may then be withdrawn from the body.

In another embodiment, extraction device may include one or more conductive coils extending between connector 364 and an electrode positioned at distal end 366. In a manner known in the art, RF ablation energy may be delivered via connector 364 to the electrode so that tissue affixed to spring 350 may be burned away using a process similar to that discussed above.

In still another embodiment, the assembly of FIGS. 6A and 6B may be used without extraction device 360. Spring 350 is deployed and retracted by moving tubular member 356 relative to lead 340. In this case, spring 350 may be a breakaway structure similar to that discussed above to facilitate chronic lead removal.

FIG. 6C is a side view of an embodiment of a lead assembly 380 that is similar to that shown in FIG. 6A, with like elements being designated with like numerical identifiers. In this embodiment, spring 382 is formed of multiple flexible strands that are affixed as by a weld or crimp to collar 352. These strands, which may be provided around the entire circumference of lead body 354, are further affixed to the distal end of tubular member 356. When tubular member is pulled in a proximal direction relative to lead body 354, the strands of spring 382 extend to be substantially parallel with the lead body as shown in FIG. 6C. This position is maintained during lead placement. An extraction device similar to extraction device 360 of FIG. 6A may be employed with tubular member, if desired.

FIG. 6D is a side view of lead assembly 380 illustrating spring 382 in a deployed state. This state is obtained by sliding tubular member 356 in a distal direction relative to lead body. The spring may be deployed a desired amount by positioning tubular member at a selected location relative to the lead body. The selected position may be retained using a removable clip or other similar fixation device.

FIG. 6E is a cross-sectional view of lead assembly 380 at line 6E-6E of FIG. 6D. This view illustrates the manner in which multiple strands of spring 382 may be positioned around the circumference of lead body 354 to form a basket-like structure when the spring is deployed.

FIG. 7A is a side view of a lead assembly 398 that is similar to the embodiment shown in FIGS. 6A and 6B. Lead assembly 398 includes a spring 402 (shown in cross-section) that may be a stent-like mesh, a coil, or some other type of expandable structure. Spring 402 is retained between a lead 400 and a slidable tubular member 404 (also shown in cross-section), which may take any of the forms discussed in the above-described embodiments. Proximal end 405 of spring 402 is affixed to an outer surface of lead 400 using a medical grade adhesive layer 407.

Distal movement of tubular member 404 is limited by a first stopper 406 located at a distal end of lead 400. Similarly, proximal movement is limited by a second stopper 408 located somewhat distal to connector sleeve 409. Tubular member 404 includes a conductive ring 410 coupled to its distal end. Conductive ring 410 is electrically coupled to conductive coil 412, which is, in turn, is electrically coupled to a ring connector 414 located at a proximal end of tubular member.

FIG. 7A illustrates spring 402 in an un-deployed state as is used to implant lead 400. In this position, lead 400 and tubular member 404 may be delivered to an implant site using a guide catheter and/or a stylet or guidewire 420 that is inserted within an inner lumen (not shown) of lead 400.

FIG. 7B is a side view of lead assembly 398 including spring 402 in a fully deployed state. Spring is deployed by pulling tubular member 404 in a proximal direction relative to lead 400, as shown by arrow 422. Spring 402 is fully deployed when ring connector 414 of tubular member rests against stopper 408. If desired, spring 402 may be partially deployed by positioning ring connector 414 so that it is spaced distally from stopper 408. This position may be retained using a removable clip or another fixation member.

Lead 400, which includes a tip electrode 424, may be unipolar or multi-polar. In multi-polar embodiments, spring may be conductive, and may be electrically coupled to a ring connector of lead 400 (not shown) to serve as an anode. Alternatively, lead 400 may include a ring electrode. According to another aspect of the invention, spring 402 may include a fluorovisible material to aid a physician in determining the extent of deployment.

The current embodiment provides means for chronic lead removable. When lead extraction is performed, ring connector 414 is coupled to a source of laser energy so that coil 412 and conductive ring 410 are energized. The laser energy transmitted by ring 410 removes tissue affixed to spring 402. Tubular member 404 may be gradually slid along the length of spring 402 to its distal end 426 while conductive ring 410 delivers laser energy to remove affixed tissue. This process frees the spring from the tissue so that a safe lead extraction procedure may be completed.

The foregoing embodiments of the invention provide a lead assembly including a deployable fixation mechanism. The fixation mechanism may be expanded a selectable amount based on the size of the surrounding body structure. Furthermore, the fixation mechanism is retractable, as may be required when the lead assembly must be moved to a new implant site. The invention provides additional advantages by providing means for facilitating chronic lead removal.

Although the disclosed embodiments of the invention were described as being primarily for use within vessels, including the venous and arterial anatomy such as the coronary sinus and branch veins, these embodiments may also be adapted for implantation within a chamber of the heart such as the right atrium or right ventricle. The concepts described herein may also be employed within a left chamber of the heart, as may be accomplished by piercing a septal wall. The invention may further be employed by systems and methods adapted to treat neurological disorders. Any other type of system or method for implanting a device within a body structure may usefully apply the concepts set forth in reference to the current invention. Thus, the above-described structures and methods of use are to be considered merely exemplary, and not limiting.

What is claimed is:

1. A lead assembly for implanting within a body, comprising:
a lead body; and
a spring member adjacent to the lead body having proximal and a distal ends and biased to expand away from the lead body, the spring member selectively deployable in one of a first deployed state maintaining the lead body in a fixed location relative to the body, and a second deployed state enabling passage of the lead body within the body;
a collar slidably engaging the lead body and the spring member and holding it compressed against the lead body, the collar positionable along the lead body and along the spring member to couple to the spring member at selected locations between its proximal and distal ends and to thereby deploy the spring member by selectable amounts.

2. The lead assembly of claim 1, wherein the spring member is an expandable coil.

3. The lead assembly of claim 1, wherein the spring member is an expandable mesh.

4. The lead assembly of claim 2, wherein a portion of spring member is affixed to the lead body.

5. The lead assembly of claim 4, and further including a removable fixation member to maintain the tubular member at a desired position relative to the lead body.

6. A lead assembly for implanting within a body, comprising:
a lead body; and
a spring member adjacent to the lead body, the spring member selectively deployable in one of a first deployed state maintaining the lead body in a fixed location relative to the body, and a second deployed state enabling passage of the lead body within the body;

wherein the spring member includes multiple weakened joints each being designed to fracture when sufficient force is exerted on the tubular member, whereby the spring member is separated from the lead assembly.

7. The lead assembly of claim 1, wherein at least a portion of the spring member is formed of a conductive material to serve as an electrode.

8. The lead assembly of claim 1, wherein the spring member is formed, at least in part, of a fluorovisible material.

9. The lead assembly of claim 1 wherein the spring member includes a lumen adapted to receive a stiffening member, the collar being positionable along the portion of the lead body by advancing the stiffening member within the lumen.

10. The lead assembly of claim 1, wherein the collar is coupled to the proximal end of the spring member, and wherein the collar may be moved in a proximal direction relative to the lead body a selectable amount to deploy the spring member.

11. The lead assembly of claim 1, wherein the lead body includes a lumen to receive a stiffening member.

12. The lead assembly of claim 11, wherein the lead body includes a distal end carrying a tip electrode.

13. The lead assembly of claim 1, and further including a tubular member slidably engaging at least a portion of the lead body, and being positionable relative to at least a portion of spring member to maintain the spring member in an unexpanded state.

14. The lead assembly of claim 13, wherein the tubular member may be repositioned relative to the lead body and to the spring member to deploy spring member a selectable amount.

15. The lead assembly of claim 14, and further including a coupling member to maintain tubular member in a desired positioned relative to the lead body.

16. The lead assembly of claim 15, and further including a stopper to restrict movement of the tubular member relative to the lead body.

17. A lead assembly for implanting within a body, comprising:

a lead body; and a spring member adjacent to the lead body, the spring member selectively deployable in one of a first deployed state maintaining the lead body in a fixed location relative to the body, and a second deployed state enabling passage of the lead body within the body;

wherein the tubular member may be positioned relative to the lead body and to the spring member to allow spring member to be released from the lead assembly into the body.

18. The lead assembly of claim 4, and further including an extraction device positioned adjacent to the tubular member to deliver energy to tissue affixed to the spring member during chronic removal of the lead assembly.

19. The lead assembly of claim 1, and further including a rotating member rotatably mounted to the lead body and coupled to the spring member, and wherein spring member is deployed by rotating the rotating member a selectable amount relative to the lead body.

20. The lead assembly of claim 19, wherein the spring member is adapted to be wound around, and in relatively close proximity to, the lead body when the spring member is not deployed.

* * * * *